US009435817B2

(12) United States Patent
Benchikh et al.

(10) Patent No.: US 9,435,817 B2
(45) Date of Patent: Sep. 6, 2016

(54) DETECTION OF SYNTHETIC CANNABINOIDS

(75) Inventors: Elouard Benchikh, Crumlin (GB); Stephen Peter Fitzgerald, Crumlin (GB); Paul John Innocenzi, Crumlin (GB); Philip Andrew Lowry, Crumlin (GB); Ivan Robert McConnell, Crumlin (GB)

(73) Assignee: Randox Laboratories Limited, Crumlin (GB)

( * ) Notice: Subject to any disclaimer, the term of this patent is extended or adjusted under 35 U.S.C. 154(b) by 590 days.

(21) Appl. No.: 13/585,630

(22) Filed: Aug. 14, 2012

(65) Prior Publication Data
US 2013/0065323 A1 Mar. 14, 2013

Related U.S. Application Data

(63) Continuation-in-part of application No. 13/332,042, filed on Dec. 20, 2011, now Pat. No. 8,906,633.

(30) Foreign Application Priority Data

Feb. 14, 2011 (GB) .................................. 1102544.2
Jun. 21, 2011 (GB) .................................. 1110425.4

(51) Int. Cl.
*C07K 16/16* (2006.01)
*G01N 33/94* (2006.01)
*C07K 16/44* (2006.01)
*C07K 17/14* (2006.01)

(52) U.S. Cl.
CPC ............. *G01N 33/948* (2013.01); *C07K 16/44* (2013.01); *C07K 17/14* (2013.01)

(58) Field of Classification Search
None
See application file for complete search history.

(56) References Cited

U.S. PATENT DOCUMENTS

| 5,248,611 | A | * | 9/1993 | Benkovic et al. ............ 435/280 |
| 5,817,766 | A | | 10/1998 | Hui et al. |
| 6,900,236 | B1 | | 5/2005 | Makriyannis et al. |
| 8,906,633 | B2 | | 12/2014 | Benchikh et al. |
| 2013/0066053 | A1 | | 3/2013 | Fitzgerald et al. |
| 2013/0196354 | A1 | | 8/2013 | Fitzgerald et al. |
| 2015/0118763 | A1 | | 4/2015 | Fitzgerald et al. |

FOREIGN PATENT DOCUMENTS

| EP | 0736529 A1 | 3/1996 |
| EP | 2487155 A1 | 8/2012 |
| WO | 0273214 A2 | 9/2002 |
| WO | 2010127452 A1 | 11/2010 |

OTHER PUBLICATIONS

C. V. Rao, "Immunology,. A textbook", Alpha Science Internatl. Ltd., 2005, pp. 63, 69-71.*
Weissman et al., "Cannabimimetic activity from CP-47,497, a derivative of 3-phenylcyclohexanol," J. Pharmacol. Exp. Ther., 1982, vol. 223, No. 2, pp. 516-523.*
Wild, "The Immunoassay Handbook," Third Ed., Elsevier, 2005, pp. 255-256.*
Melvin et al., "A cannabinoid derived prototypical analgesic," J. Med. Chem., 1984, vol. 27, No. 1, pp. 67-71.*
Dresen, S. et al., "Monitoring of Herbal Mixtures Potentially Containing Synthetic Cannabinoids as Psychoactive Compounds," J. Mass. Spectrometry, 2010, pp. 1186-1194, vol. 45.
Goodrow, M.H. et al., "Strategies for Immunoassay Hapten Design," in Immunoanalysis of Agrochemicals; Nelson, J. et al., ACS Symposium Series, 1995, Chapter 9, pp. 119-139, vol. 586.
Hudson, S. et al., "Use of High-Resolution Accurate Mass Spectrometry to Detect Reported and Previously Unreported Cannabinomimetics in 'Herbal High' Products," J. Anal. Toxicol., 2010, pp. 252-260, vol. 34.
Huffman, J. et al., "1-Pentyl-3-phenylacetylindoles, a New Class of Cannabimimetic Indoles," Bioorganic & Medicinal Chemistry Letters, 2005, pp. 4110-4113, vol. 15.
Kraemer, T., "V10—Studies on the Metabolism of JWH-18, the Pharmacologically Active Ingredient of Different Misused Incenses," Abstracts—Vortrage Hauptsymposium, 2008, pp. 90, vol. 76, No. 2.
Liu, Y. et al., "Design and Synthesis of AX4697, a Bisindolylmaleimide Exo-affinity Probe that Labels Protein Kinase C Alpha and Beta," Bioorganic & Medicinal Chemistry Letters, 2008, pp. 5955-5958, vol. 18.
Möller, I. et al., "Screening for the Synthetic Cannabinoid JWH-018 and Its Major Metabolities in Human Doping Controls," Drug Testing and Analysis, 2011, pp. 609-620, vol. 3.
Rana, S. et al., "Routine Screening of Human Urine for Synthetic Cannabinoids by LC-MS/MS Utilizing Spectrum Based Library Search," Redwood Toxicology Laboratory, SOFT 2010. (Abstract).
Singh, P. et al., "Synthesis and Evaluation of Indole-based New Scaffolds for Antimicrobial Activities—Identification of Promising Candidates," Bioorganic & Medicinal Chemistry Letters, 2011, pp. 3367-3372, vol. 21.
Sobolevsky, T., "Detection of JWH-018 Metabolites in Smoking Mixture Post-Administration Urine," Forensic Science International, 2010, pp. 141-147, vol. 200.
Uchiyama, N. et al., "Chemical Analysis of Synthetic Cannabinoids as Designer Drugs in Herbal Products," Forensic Science International, 2010, pp. 31-38, vol. 198.
Wintermeyer, A. et al., "In vitro Phase I Metabolism of the Synthetic Cannabimimetic JWH-018," Anal. Bioanal. Chem., 2010, pp. 2141-2153, vol. 398.
Zhao, D. et al., "Synthesis of Phenol, Aromatic Ether, and Benzofuran Derivatives by Copper-Catalyzed Hydroxylation of Aryl Halides," Angew. Chem. Int. Ed., 2009, pp. 8729-8732, vol. 48, Issue 46.

(Continued)

*Primary Examiner* — Galina Yakovleva
(74) *Attorney, Agent, or Firm* — Saul Ewing LLP; Kathryn Doyle; Domingos J. Silva

(57) ABSTRACT

The invention describes methods and kits for detecting and determining current and future synthetic cannabinoids from the CP family. Unique antibodies derived from novel immunogens enable said methods and kits.

2 Claims, 6 Drawing Sheets

(56) References Cited

OTHER PUBLICATIONS

Randox Toxicology, Product List 2012, pp. 1-43.
Watanabe, K., et al., "Cross-Reactivity of Various Tetrahydrocannabinol Metabolites with a Monoclonal Antibody against Tetrahydrocannabinolic Acid," Journal of Health Science, (2000), vol. 46, No. 4, pp. 310-313.
Tanaka, H., et al., "Monoclonal antibody against tetrahydrocannabionolic acid distinguishes Cannabis sativa samples from different plant species," Forensic Science International (1999), vol. 106, pp. 135-146.
Salamone, S., et al., "A Non-Cannabinoid Immunogen Used to Elicit Antibodies with Broad Cross-Reactivity to Cannabinoid Metabolites," Journal of Forensic Sciences, pp. 821-826, 1998, vol. 43, No. 4.
Tanaka, H., "Immunochemical Approach Using Monoclonal Antibody against •9-TetrahydrocannabinolicAcid (THCA) to Discern Cannabis Plants and to Investigate New Drug Candidates," Current Drug Discovery Technologies, (2011) vol. 8, pp. 3-15.
Dresen, S., et al., "Development and validation of a liquid chromatography—tandem mass spectrometry method for the quantitation of synthetic cannabinoids of the aminoalkylindole type and methanandamide in serum and its application to forensic samples," J. Mass Spectrom, (2011), vol. 46, pp. 163-171.
Logan, B., et al., "Technical Bulletin: NMS Labs test for JWH-018, JWH-019, JWH-073, JWH-250 and AM-2201 Primary Monohydroxy Metabolites in Human Urine," NMS Labs, (2011), pp. 1-5.
Logan, B., et al., "Identification of Synthetic Cannabinoids in Herbal Incense Blends in the United States," Forensic Sciences, (2012), vol. 57, No. 5, pp. 1168-1180.
De Jager, A.D. et al., "LC-MS/MS Method for the Quantitation of Metabolites of Eight Commonly-Used Synthetic Cannabinoids in Human Urine—An Australian Perspective," Journal of Chromatography B, vol. 897, pp. 22-31, 2012.

* cited by examiner

CP47,497 (C₇)

CP47,497 (C₈)

CP47,497 (C₇) CMO (Hapten - 1)

CP47,497 (C₈) CMO (Hapten - 2)

DETECTION OF SYNTHETIC CANNABINOIDS

CROSS-REFERENCE TO RELATED APPLICATIONS

The present application is a continuation-in-part of, and claims priority to, U.S. application Ser. No. 13/332,042, filed Dec. 20, 2011, now issued as U.S. Pat. No. 8,906,633, which claims priority to GB Patent Applications No. 1102544.2, filed Feb. 14, 2011, and No. 1110425.4, filed Jun. 21, 2011, all of which applications are incorporated herein by reference in their entireties.

BACKGROUND

The increasing rise in the use of stealth drugs (novel synthetic drugs that were previously or remain analytically/structurally uncharacterised and unclassified by government institutions), is exemplified by synthetic cannabinoid products which incorporate CP 47,497 as the active ingredient. Stealth synthetic cannabinoid (SSC) drug manufacturers can base their choice of active molecular target on scientific literature studies that address the therapeutic potential of $CB_1$ (the CNS cannabinoid receptor) agonists and antagonists. By incorporating novel, analytically uncharacterised compounds with high $CB_1$ receptor affinity into herbal mixtures (packaged under such names as Spice, Yucatan Fire), the manufacturers are able to target drug consumers clandestinely by promoting the material as herbal therapeutics. A problem for governments and drug enforcement agencies is that, even after identifying and banning a new synthetic cannabinoid, the manufacturers can rapidly react to the banning by incorporating a different active analogue into the same or a different herbal product; targeted minor changes in the molecular structure of the known active compound can preserve receptor activity but often produces a molecule whose GC-MS/LC-MS (the commonly applied detection techniques) profile is completely different from the original active molecule. Hence, the new active molecule initially remains unidentified and a further resource intensive and costly chemical analytical study to enable structural characterisation is required. The main active ingredients highlighted in SSC products to date are JWH-018, CP 47,497 and JWH-073 (Uchiyama et al. 2010; Hudson et al. 2010; Dresen et al. 2010). Initial studies of the metabolism of CP compounds have highlighted metabolic processes similar to tetrahydrocannabinol (THC) metabolism, namely ring and alkyl substituent hydroxylation, carboxylation and glucuronidation. As described herein, unless otherwise stated, CP refers to synthetic cannabinoid molecules comprising the unfused bicyclic structure II, in which X is either ethyl, n-propyl or n-butyl, as well as, metabolites thereof

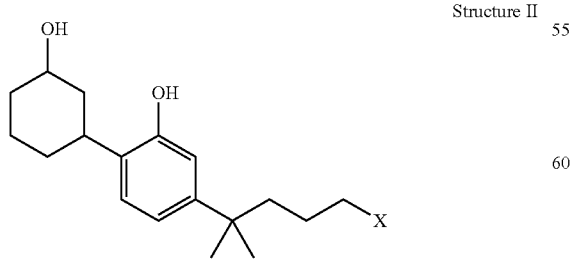

Structure II

Herbal therapeutics have been analysed using solvent extraction, pre-derivatisation and finally GC-MS analysis in SIM mode (Rana et al. 2010). This method is inadequate for the detection of future and 'current' JWH and CP SSCs (it is conceivable that 'current' herbal therapeutics, as well as CP 47,497, incorporate CP SSCs that are not yet characterised), requires sample pre-derivatisation, specialist staff for its implementation and expensive equipment. In order to address the problem associated with the cheap and rapid detection of known CP molecules and their metabolites and/or future and associated metabolites based on the CP drug families, the Inventors devised a novel method based on novel antibodies raised from novel immunogens. The antibodies underpin an effective analytical and economic solution to the detection and quantification of current and future CP $CB_1$-active molecules in in vitro patient samples and herbal therapeutics.

SUMMARY OF THE INVENTION

The invention describes a rapid and practical method for the detection and determination of known and/or stealth synthetic cannabinoids based on the CP drug family. Kits and their use for CP SSC detection and determination in herbal therapeutics and in vitro patient samples are also described. The invention is underpinned by novel immunogens and antibodies which enable said methods, kits and applications.

DETAILED DESCRIPTION OF THE INVENTION

Figure 1:
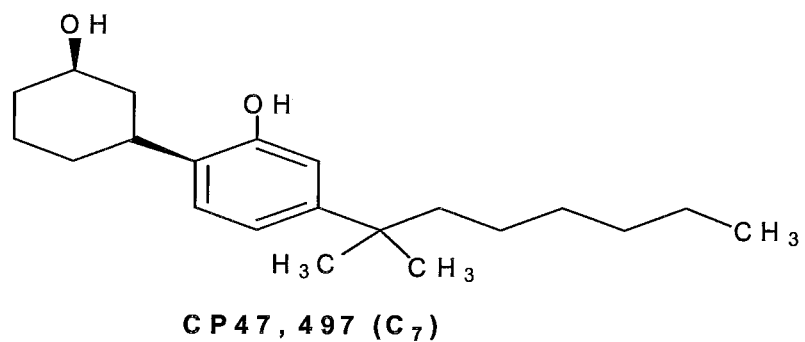
FIG. 1 contains diagrams of chemical structures of CP47, 497 ($C_7$ & $C_8$). $C_7$ is used to denote a compound of structure II in which X is n-propyl and $C_8$ is used to denote a compound of structure II in which X is n-butyl.
Figure 1:
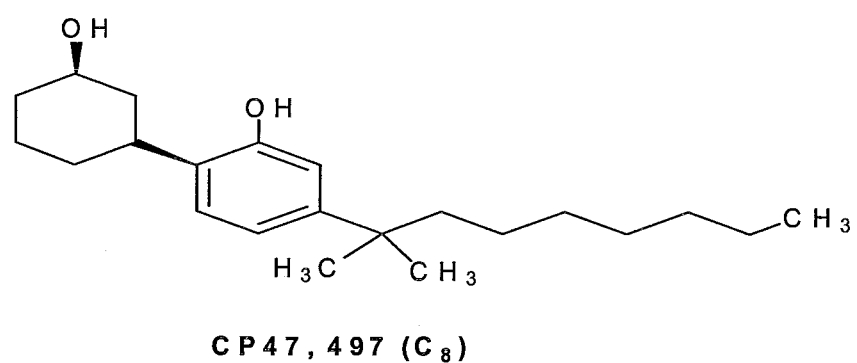
Figure 2:
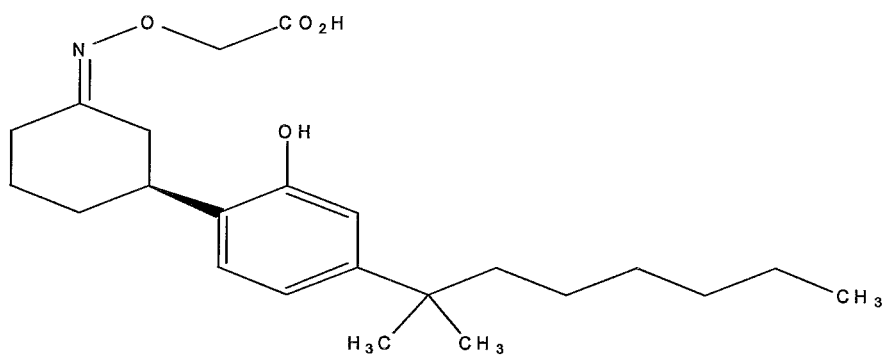
FIG. 2 contains diagrams of chemical structures of CP47, 497 ($C_7$ & $C_8$) Haptens.
Figure 2:
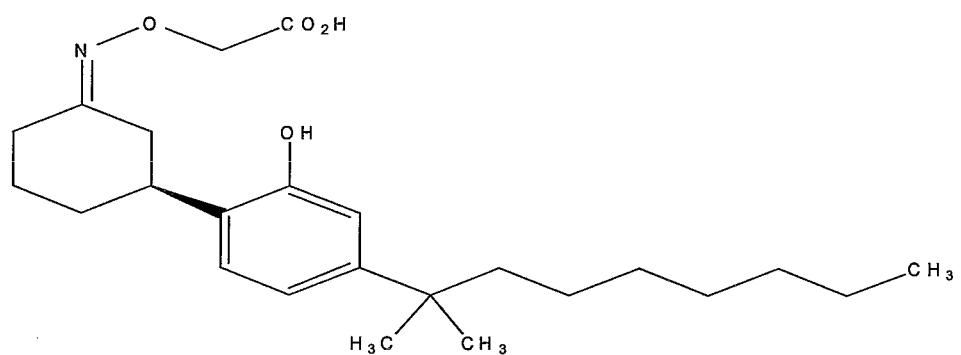

In a first aspect of the invention, there is provided an antibody which binds to an epitope of structure:

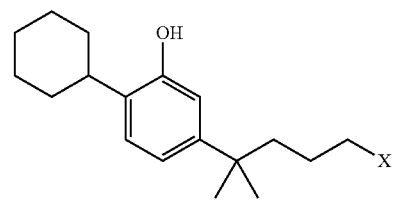

wherein X is selected from n-propyl and n-butyl. The definition of X is intended to embrace the CP-47,497 ($C_7$ homologue) and the CP-47,497 ($C_8$ homologue).

Optionally, there are 2 hydrogen substituents at position 6 of the cyclohexyl ring in the above-mentioned epitope.

Optionally, there is a hydrogen substituent at position 4 of the phenyl ring in the above-mentioned epitope.

Optionally, there is a hydrogen substituent at position 3 of the phenyl ring in the above-mentioned epitope.

Optionally, the antibody of first aspect of the invention binds to an epitope selected from the group consisting of a racemic mixture of (±)-CP-47,497 ($C_7$ homologue), a racemic mixture of (±)-CP-47,497 ($C_8$ homologue), a stereoisomer of CP-47,497 ($C_7$ homologue) and a stereoisomer of CP-47,497 ($C_8$ homologue).

Optionally, the antibody of first aspect of the invention is further characterised by having a $B/B_0$ of ≤50% for the epitope of claim 4 (standardised with (±)-CP-47,497 ($C_8$ homologue) and using tracer 1 ($C_7$).

Optionally, the antibody of the first aspect of the invention is further characterised by being raisable against one or more immunogens of the following structures

GROUP II (E)-(H)

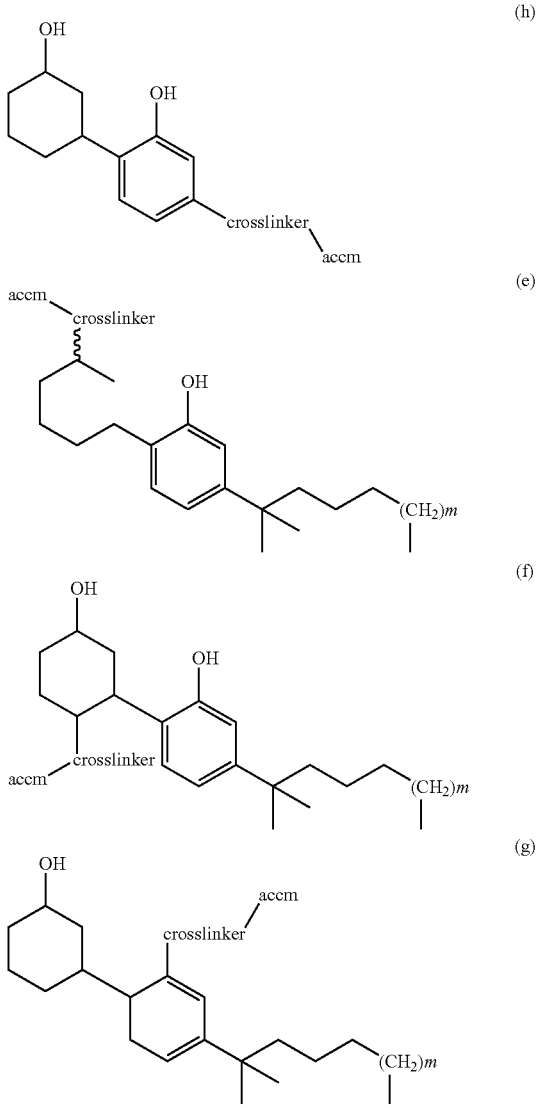

in which the accm is an antigenicity conferring carrier material; the crosslinker is a functionalised linking group joining the accm to the remainder of the molecule, the crosslinker of structure (e) forming either a single or double bond to the cyclohexyl ring and the crosslinker of structure (c) extending from the 4, 5, 6 or 7-position of the indole ring.

Optionally, the antibody is raisable against the immunogen of structure (e) and having a $B/B_0$ of ≤50% (standardised with (+)-CP-47,497 ($C_8$ homologue) and using tracer 1 ($C_7$).

Further optionally, the antibody is raisable against the immunogen of structure (e) in which m=1-3, the crosslinker is either -(L)$_p$-M-Q- or =N—O-M-Q- in which Q, which is attached to the accm, is chosen from carbonyl, amino, thiol, maleimide, isocyanato, isothiocyanato, aldehyde, diazo and dithiopyridyl, M is a $C_{1-10}$ substituted or unsubstituted straight chain alkylene or arylene moiety, p=0 or 1 and L is O, NH, S, ester, thioester, or amide.

Still further optionally, the antibody is raisable against the immunogen of structure (e) in which m=1-2, the crosslinker is =N—O-M-Q- in which Q, which is attached to the accm, is chosen from carbonyl, amino, thiol, maleimide, isocyanato, isothiocyanato, aldehyde, diazo and dithiopyridyl and M is a $C_{1-10}$ substituted or unsubstituted straight chain alkylene or arylene moiety.

Still further optionally, the antibody is raisable against the immunogen of structure (e) in which the crosslinker is =N—O-M-Q- in which Q, which is attached to the accm, is carbonyl and M is a $C_1$ alkylene moiety.

Optionally, the antibody is raisable against the immunogen of structure (e), in which the immunogen of structure (e) is selected from the group consisting of

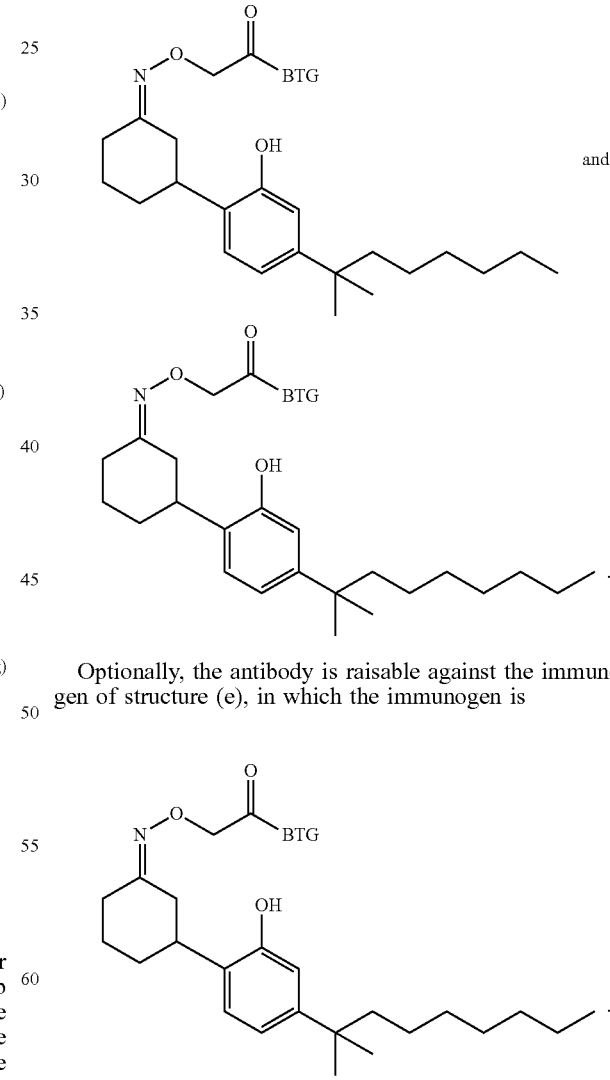

Optionally, the antibody is raisable against the immunogen of structure (e), in which the immunogen is In a second aspect of the invention there is provided a method of detecting or determining synthetic cannabinoids of the CP family and/or one or more metabolites thereof in an in vitro sample of an individual or in a solution derived from a substance suspected of containing synthetic cannabinoids, comprising contacting the sample or solution with one or more detecting agents and one or more antibodies of the first aspect of the invention; detecting, or determining the quantity of, the one or more detecting agents; and deducing from calibrators, the presence of or amount of a molecule or molecules of the CP family and/or metabolites thereof in the sample or solution.

In a third aspect of the invention, there is provided a kit for detecting or determining a molecule or molecules of the CP family and/or one or more metabolites thereof, comprising one or more antibodies of the first aspect of the invention.

The invention also discloses one or more immunogens possessing the following structures

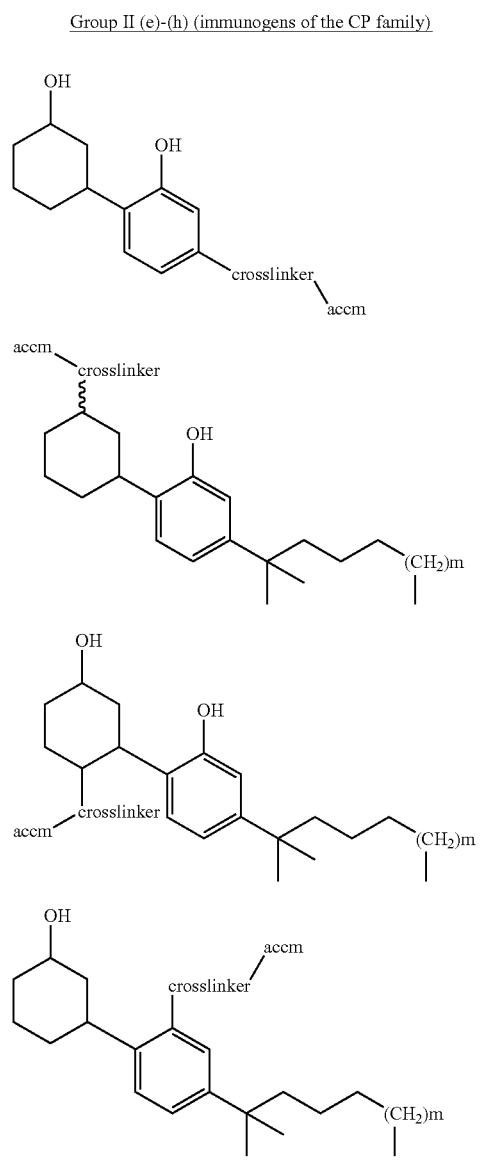

in which the accm is an antigenicity conferring carrier material; m is 1-3; and the crosslinker is a functionalised linking group joining the accm to the remainder of the molecule.

By "functionalised", it is meant the crosslinker incorporates atoms that enable it to bond to both the accm and the CP moiety, forming a bridging group. In structure (e) the crosslinker forms either a single or double bond to the cyclohexyl ring. The crosslinker concept is well known to the person skilled in immunogen synthesis. For the current invention, when conjugating the hapten to the accm to form the immunogen, the nature and length of the crosslinker follows standard methods in order to optimise hapten epitopic recognition by the antibody. This entails a crosslinker of low immunogenicity and a chain length preferably of no greater than about ten atoms, most preferably no greater than six atoms.

Preferably for structures (f) and (h) the crosslinker is -$(A)_n$-D-Y— where A=O, —N(R)—, S, —S(O)— (sulphoxide) or —$S(O)_2$— (sulphonyl) and R=H or $C_{1-5}$ alkyl, n=0 or 1 and D is a $C_{1-10}$, preferably a $C_{1-5}$ substituted or unsubstituted straight chain alkylene or arylene moiety and Y, which is attached to the accm, is selected from groups such as carbonyl, amino, thiol, maleimide, isocyanato, isothiocyanato, aldehyde, diazo and dithiopyridyl. Y is preferably carbonyl or amino.

Preferably for structure (e) m=2 or 3, the crosslinker is either -$(L)_p$-M-Q- or =N—O-M-Q- in which Q, attached to the accm, is either carbonyl or amino, M is a $C_{1-10}$, preferably a $C_{1-5}$ substituted or unsubstituted straight chain alkylene or arylene moiety, p=0 or 1 and L is O, NH, S, ester, thioester, or amide. More preferably, for structure (e) m=2 or 3, the crosslinker is =N—O-M-Q-, in which the crosslinker comprises =N—O—$CH_3$—COOH before attachment to the accm and =N—O—$CH_3$—CO— after attachment to the accm by an amide link.

Preferably for structure (g) m=2 or 3, the crosslinker is -$(L)_p$-M-N— in which N, attached to the accm, is either carbonyl or amino, M is a $C_{1-10}$, preferably a $C_{1-5}$ substituted or unsubstituted straight chain alkylene or arylene moiety, p=0 or 1 and L is O, NH, S, ester, thioester, or amide.

The skilled person is aware that, for these antibodies to recognize CP molecules, they must bind to particular structures or epitopes of the hapten (in this context the hapten being that part of the immunogen that is not the crosslinker or accm); the epitopes are often distinct groups incorporating functional groups.

Another aspect of the invention is an antibody raisable against an immunogen of structure (e), (f), (g) or (h), the antibody being able to bind to molecules of the CP family, metabolites of CP molecules and future SSC molecules comprising structure II. Optionally, the antibody is raisable against an immunogen of structure (e), the antibody being able to bind to molecules of the CP family, metabolites of CP molecules and future SSC molecules comprising structure II. When used in reference to an antibody, the word specific in the context of the current invention refers to the analyte that is preferably bound by the antibody, as gauged by a suitable metric such as the $IC_{50}$. Given the $IC_{50}$ of various analytes their cross-reactivities can be calculated.

The antibody can either be a polyclonal or monoclonal antibody using well-known methods. If the polyclonal antibody possesses the required specificity and sensitivity, that is, it binds a single analyte within the detection range of the assay, development of a monoclonal antibody is unnecessary.

One or more antibodies of the invention can be incorporated into a kit for the detection and semi-determination of individual or multiple SSCs. The skilled person in the immunodiagnostic field is aware of several alternative immunoassay formats that could incorporate the antibodies of the invention either in solution or tethered (e.g. covalently bonded or electrostatically 'non-bonded' through Van der Waal's forces) to a solid substrate such as beads, glass/plastic slides or ceramic chips (a chip defined as a small, planar substrate). A preferred solid substrate onto which the antibodies of the invention are covalently bonded is a chip, preferably a ceramic chip; the word 'Biochip'™ can be used to refer to a chip with antibodies attached. Such a "biochip" is described in EP1273349, incorporated herein by reference its entirety. Thus the invention also provides a solid substrate, preferably a biochip, comprising antibodies raisable against an immunogen of one or more of structures (e), (f), (g) or (h), the antibodies being able to bind to an epitope of one or more molecules of the CP family and/or one or more metabolites thereof. Optionally, the invention further provides a solid substrate, preferably a biochip, comprising antibodies raisable against an immunogen of structure (e), the antibodies being able to bind to an epitope of one or more molecules of the CP family and/or one or more metabolites thereof.

The detection and determination criteria for a SSC using an immunoassay platform includes, as is well-known in the art, exceeding a pre-defined cut-off/concentration value or measuring the calibrator equivalent value as derived from a calibrator curve (also referred to as a standard curve).

Classification of immunoassays depends on whether one (noncompetitive) or two (competitive) antigens are used:

1. Competitive, homogeneous immunoassay

The antigen in the unknown sample competes with labeled antigen to bind with antibodies. The amount of unbound, labeled antigen is then measured, which is directly proportional to the concentration of sample antigen.

2. Competitive, heterogeneous immunoassay

The antigen in the unknown sample competes with labeled antigen to bind with antibodies. The amount of labeled antigen bound to the antibody site is then measured. In this method, the response will be inversely related to the concentration of antigen in the unknown.

3. One-site, noncompetitive immunoassay

The unknown antigen in the sample binds with labeled antibodies. The unbound, labeled antibodies are washed away, and the bound, labeled is measured, which is directly proportional to the amount of unknown antigen.

4. Two-site, noncompetitive immunoassays

The antigen in the unknown sample is bound to the antibody site, then labeled antibody is bound to the antigen. The amount of labeled antibody on the site is then measured. It will be directly proportional to the concentration of the antigen because labeled antibody will not bind if the antigen is not present in the unknown sample. This type is also known as sandwich assay as the antigen is "sandwiched" between two antibodies.

Another aspect of the invention is a method of detecting or determining synthetic cannabinoids of the CP family and their metabolites in an in vitro sample of an individual or in a solution derived from a substance suspected of containing synthetic cannabinoids comprising: contacting the sample or solution with one or more detecting agents and one or more antibodies of the invention that bind to molecules of the CP family, and detecting or determining, by reference to calibrators, the presence or concentration of a molecule or molecules of the CP family. Optionally, the method further comprises a step of measuring the detecting agents before detecting or determining, by reference to calibrators, the presence or concentration of a molecule or molecules of the CP family. The detecting agents measuring step can be measuring detecting agent bound to the antibodies, the detecting agent being labeled antigen in a competitive, homogeneous immunoassay in which unbound, labeled antigen is measured. Alternatively, the detecting agents measuring step can be measuring detecting agent bound to the antibodies, the detecting agent being labeled antigen in a competitive, heterogeneous immunoassay in which bound, labeled antigen is measured. Further alternatively, the detecting agents measuring step can be measuring detecting agent bound to the antibodies, the detecting agent being labeled antibodies in a one-site, noncompetitive immunoassay in which bound, labeled antibodies are measured. Still further alternatively, the detecting agents measuring step can be measuring detecting agent bound to the antibodies, the detecting agent being labeled antibody that is bound to the antigen that is, in turn, also bound to the antibody.

With reference to 'detecting or determining', 'detecting' means qualitatively analyzing for the presence or absence of a substance, 'determining' means quantitatively analyzing for the amount of a substance.

Optionally, the detecting agent is a small molecule, generally of similar structure to a molecule to be detected conjugated to a labelling agent, the detecting agent being able to bind to one of the antibodies of the invention.

The labelling agent is selected from an enzyme, a luminescent substance, a radioactive substance, or a mixture thereof. Preferably, the labelling agent is an enzyme, more preferably a peroxidase, most preferably horseradish peroxidase (HRP). Alternatively, or additionally, the luminescent substance may be a bioluminescent, chemiluminescent or fluorescent material.

For the purposes of the invention, the patient sample to be used for in vitro analysis can be hair or a peripheral biological fluid but is preferably whole blood, serum, plasma, or urine.

When referring to the detection or determination of a CP molecule, with or without a suffixed number attached to CP, the metabolite or metabolites are also inferred unless otherwise stated.

The invention also describes kits for detecting or determining a molecule or molecules of the CP family comprising one or more antibodies of the invention. Preferably, the kit comprises one or more antibodies raisable against an immunogen of structure (e), (f), (g) or (h) of Group II. More preferably, the kit comprises one or more antibodies raisable against an immunogen of structure (e) of Group II.

The antibodies of the kit are preferably tethered to any suitable solid support such as a chip. Although the solid support can be of any suitable shape such as a bead or a slide and of any suitable material such as silicon, glass or plastic, the solid support is preferably a ceramic chip.

The kit may further include calibrators and one or more detecting agents and optionally includes instructions for the use of the antibodies of the kit and if incorporated, the calibrators and detecting agents, for detecting and determining molecules from the CP family.

The invention also embodies solid supports comprising the novel antibodies of the present invention.

The antibodies of the invention are used for the detection or determination of CP molecules either in herbal mixtures, an in vitro sample taken from an individual or any other substance suspected of their incorporation.

General Methods, Examples and Results

Preparation of Haptens, Immunogens and Detecting Agents

Although haptens provide defined structural epitopes, they are not in themselves immunogenic and therefore need to be conjugated to carrier materials, which will elicit an immunogenic response when administered to a host animal.

Appropriate carrier materials commonly contain poly(amino acid) segments and include polypeptides, proteins and protein fragments. Illustrative examples of useful carrier materials are bovine serum albumin (BSA), egg ovalbumin, bovine gamma globulin, bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen.

The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof.

Immunogen formation for the invention described herein involves conventional conjugation chemistry. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS).

General Procedure for MALDI-TOF Analysis of Immunogens.

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of sinapinic acid and bovine serum albumin (Fluka) was used as an external calibrant.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunising an animal, preferably a mammalian animal, by repeated administration of an immunogen. The serum from the immunised animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate such as a polystyrene solid support or a ceramic chip. The antibodies can be polyclonal or monoclonal using standard techniques. The signal emitted in the immunoassay is proportionate to the amount of detecting agent bound to the antibodies which in turn is inversely proportionate to the analyte concentration. The signal can be detected or quantified by comparison with a calibrator.

EXAMPLES

Figure 3A:
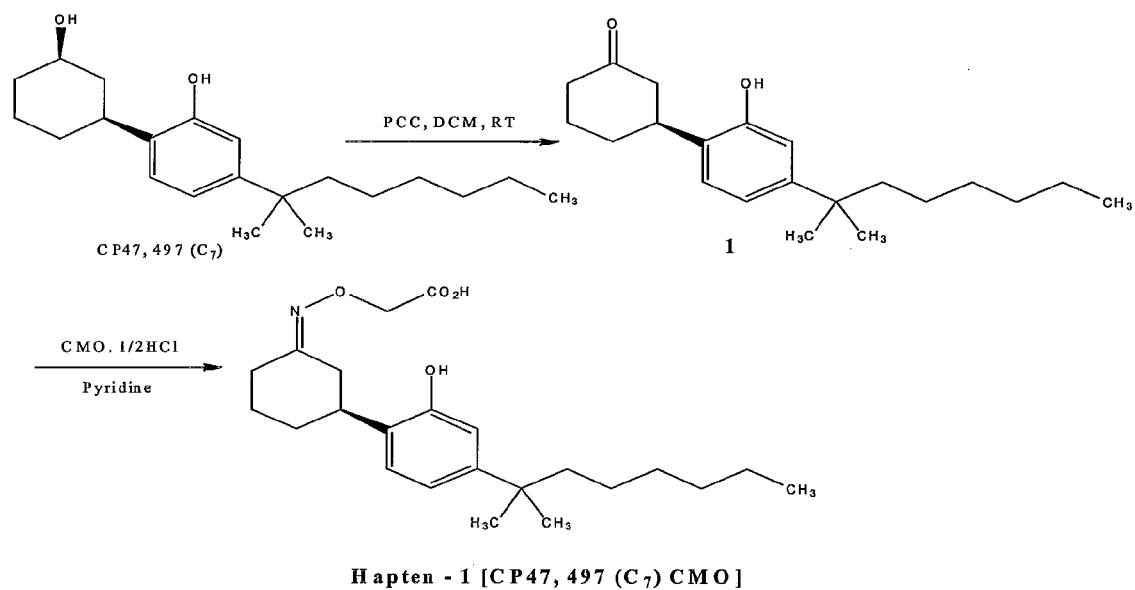
FIG. 3a contains diagrams of chemical reactions of synthesis of CP47,497 ($C_7$) Hapten 1.

Preparation of Hapten 1 (See FIG. 3a)

Example 1

Preparation of the Keto-CP47,497 ($C_7$) 1

CP47,497 ($C_7$) (CAS 70434-82-1) is supplied as a 10 mg/ml solution in methanol. First, it is transferred into 10 ml round bottom flask (165 ml, 165 mg, 0.518 mmol) and the solvent evaporated to dryness under vacuum at room temperature. Anhydrous dichloromethane (DCM) (5 ml) is added and the resulting solution is added drop-wise to a solution of pyridinium chlorochromate (PCC) (167.6 mg, 0.78 mmol) in anhydrous dichloromethane (5 ml) under stirring at room temperature (RT). The reaction mixture was stirred at room temperature for 3 hours. The reaction mixture was filtered on a pad of Celite™, washed with diethyl ether and the solvents were removed in vacuo at room temperature. The residue was dissolved in diethyl ether and taken through a small plug of silica gel, washed with diethyl ether and the solvents were removed in vacuo at room temperature to give the desired product, keto-CP47,497 ($C_7$) 1 (132 mg, 0.417 mmol, 80% yield) as a dark oil.

Example 2

Preparation of the CP47, 497 ($C_7$)-CMO (CP47,497 ($C_7$) carboxymethyloxime) (Hapten 1)

Keto-CP47,497 ($C_7$) 1 (132 mg, 0.417 mmol) was dissolved in pyridine (2 ml) and carboxymethoxylamine hemihydrochloride (CMO.½HCl) (144 mg, 1.04 mmol, 2.5 eq) was added. The reaction mixture was stirred at room temperature overnight. The solvents were evaporated, the residue was partitioned between ethyl acetate and HCl (1M) solution, the layers were separated and the organic layer was washed with brine, dried over sodium sulphate and concentrated in vacuo to give the desired product CP47,497 ($C_7$)-CMO (Hapten 1) (209 mg) as a red-brown oil that was used in the next step without further purification.

Example 3

Conjugation of CP47,497 ($C_7$)-CMO (Hapten 1) to BSA—Immunogen 1a

To a solution of CP47,497 ($C_7$)-CMO (Hapten 1) (15.00 mg, 0.0365 mM) in DMF (2.0 ml) was added EDC hydrochloride (8.85 mg, 0.0462 mM) and N-hydroxysuccinimide (5.4 mg, 0.0462 mM) and the mixture was stirred at room temperature overnight. This solution was added drop-wise to a solution of BSA (50.0 mg, 1.15 µM) in 50 mM sodium bicarbonate solution (pH 8.5) (8.0 ml). The mixture was then stirred overnight at 4° C. The solution was then dialysed against 50 mM phosphate buffer pH 7.2 (3 changes) for 24 hours at 4° C., and freeze-dried to give 43 mg of Immunogen 1a.

MALDI results showed 9.5 molecules of hapten 1 had been conjugated to one molecule of BSA.

Example 4

Figure 4:
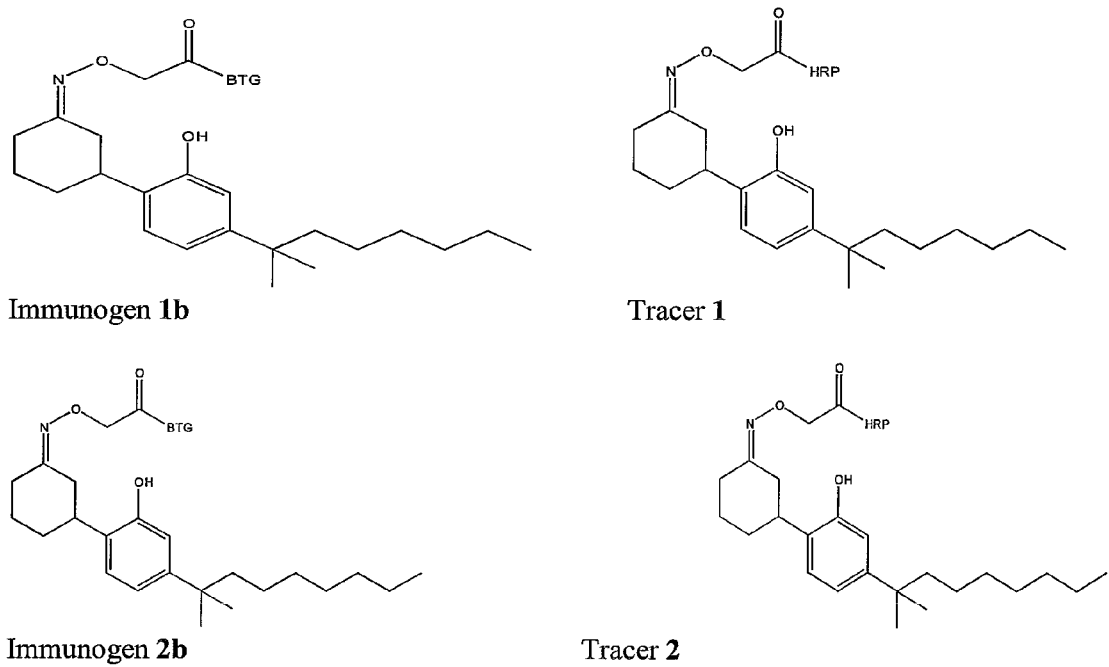
FIG. 4 contains diagrams of chemical structures of immunogens 1b and 2b and of tracers 1 and 2.

Conjugation of CP47,497 ($C_7$)-CMO (Hapten 1) to BTG—Immunogen 1b (FIG. 4)

To a solution of CP47,497 ($C_7$)-CMO (Hapten 1) (30.0 mg, 0.073 mM) in DMF (2.0 ml) was added EDC hydrochloride (17.7 mg, 0.092 mM) and N-hydroxysuccinimide (11.5 mg, 0.092 mM) and the mixture was stirred at room temperature overnight. The solution was added drop-wise to a solution of BTG (100 mg) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give 82 mg of Immunogen 1b.

Example 5

Conjugation of CP47,497 ($C_7$)-CMO (Hapten 1) to HRP (Horse Radish Peroxidase) (Tracer 1) (FIG. 4)

EDC hydrochloride (10 mg) was dissolved in water (0.5 ml) and immediately added to a solution of CP47,497 ($C_7$)-CMO (Hapten 1) (2 mg) in DMF (0.2 ml). After mixing, this solution was added drop wise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia™) in series, pre-equilibrated with PBS at pH 7.2. The hapten-HRP conjugate was then dialysed overnight against 10 L of PBS at pH 7.2 at 4° C.

Figure 3B:
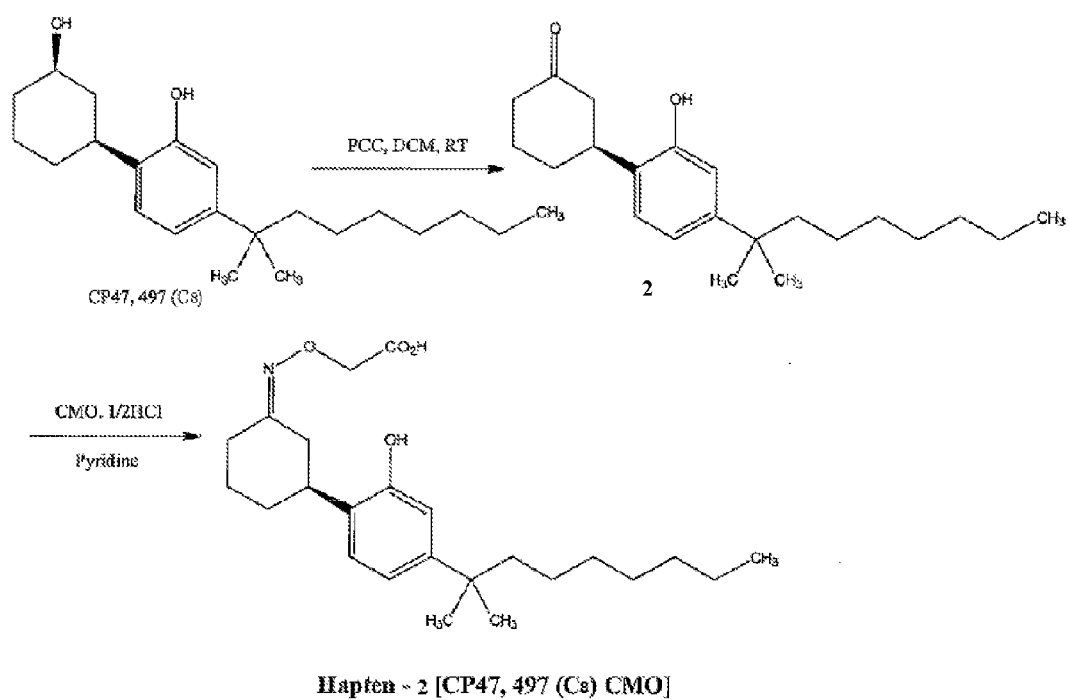
FIG. 3b contains diagrams of chemical reactions of synthesis of CP47,497 ($C_8$) (Hapten 2).

Preparation of Hapten 2 (see FIG. 3b)

Example 6

Preparation of the Keto-CP47,497 ($C_8$) 2

CP47,497 ($C_8$) (CAS 70434-92-3) is supplied as a 10 mg/ml solution in methanol. First this solution was transferred into 10 ml round bottom flask (194 ml, 194 mg, 0.583 mmol) and the solvent evaporated to dryness under vacuum at room temperature. Anhydrous dichloromethane (5 ml) is added and the resulting solution is added dropwise to a solution of pyridinium chlorochromate (188.6 mg, 0.87 mmol, 1.5 eq) in anhydrous dichloromethane (5 ml) under stirring at room temperature. The reaction mixture was stirred at room temperature for 3 hours. The reaction mixture was filtered on a pad of Celite™, washed with diethyl ether and the solvents were removed in vacuo at room temperature. The residue was dissolved in diethyl ether and taken through a small plug of silica gel, washed with diethyl ether and the solvents were removed in vacuo at room temperature to give the desired product, keto-CP47,497 ($C_8$) 2 (148 mg, 0.447 mmol, 77% yield) as a dark oil.

Example 7

Preparation of the CP47,497 ($C_8$)-CMO (Hapten 2)

Keto-CP47,497 ($C_8$) 2 (148 mg, 0.447 mmol) was dissolved in pyridine (4 ml) and CMO. ½HCl (122 mg, 1.12 mmol) was added. The reaction mixture was stirred at room temperature overnight. The pyridine was removed under high vacuum. The obtained residue was partitioned between ethyl acetate and HCl (1M) solution, the layers were separated and the organic layer was washed with brine, dried over sodium sulphate and concentrated in vacuo to give the desired product CP47,497 ($C_8$)-CMO (Hapten 2) (200 mg) as a red-brown oil that was used in the next step without further purification.

Example 8

Conjugation of CP47,497 ($C_8$)-CMO (Hapten 2) to BSA—Immunogen 2a

To a solution of CP47,497 ($C_8$)-CMO (Hapten 2) (15.5 mg, 0.0384 mM) in DMF (2.0 ml) was added EDC hydrochloride (8.85 mg, 0.0462 mM) and N-hydroxysuccinimide (5.4 mg, 0.0462 mM) and the mixture was stirred at room temperature overnight. This solution was added drop-wise to a solution of BSA (50.0 mg, 1.15 µM) in 50 mM sodium bicarbonate solution (pH 8.5) (8.0 ml). The mixture was then stirred overnight at 4° C. The solution was then dialysed against 50 mM phosphate buffer pH 7.2 (3 changes) for 24 hours at 4° C., and freeze-dried to give 40 mg of Immunogen 2a.

MALDI results showed 16.03 molecules of CP47,497 ($C_8$)-CMO (hapten 2) had been conjugated to one molecule of BSA.

Example 9

Conjugation of CP47,497 ($C_8$)-CMO (Hapten 2) to BTG—Immunogen 2b (FIG. 4)

To a solution of CP47,497 ($C_8$)-CMO (Hapten 2) (31.0 mg, 0.073 mM) in DMF (2.0 ml) was added EDC hydrochloride (17.7 mg, 0.092 mM) and N-hydroxysuccinimide (11.5 mg, 0.092 mM) and the mixture was stirred at room temperature overnight. The solution was added drop-wise to a solution of BTG (100 mg) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give 87 mg of Immunogen 2b.

Example 10

Conjugation of CP47,497 ($C_8$)-CMO (Hapten 2) to HRP (Tracer 2) (FIG. 4)

EDC hydrochloride (10 mg) was dissolved in water (0.5 ml) and immediately added to a solution of CP47,497 ($C_8$)-CMO (Hapten 2) (2 mg) in DMF (0.2 ml). After mixing, this solution was added drop wise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia™) in series, pre-equilibrated with PBS at pH 7.2. The hapten-HRP conjugate was then dialysed overnight against 10 L of PBS at pH 7.2 at 4° C.

Preparation of Antisera

In order to generate polyclonal antisera, each of Immunogens 1b and 2b of the present invention is with Freund's Adjuvant and the mixture is injected into a host animal, such as rabbit, sheep, mouse, guinea pig or horse. Sheep are the preferred host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification. However, in other cases, such as where the antibody is to be immobilised on a solid support, purification steps can be taken to remove undesired material and eliminate non-specific binding.

The specific antibodies prepared in this invention are useful as reagents in immunoassays for the detection or semi-determination of CP47,497-$C_7$ and CP47,497-$C_8$, in biological fluids.

Example 11

Preparation of antibodies to Immunogen 1b (CP47,497-$C_7$) and to Immunogen 2b (CP47,497-$C_8$)

An aqueous solution of Immunogen 1b or Immunogen 2b was formulated with Freund's Complete Adjuvant (FCA) to form an emulsion consisting of 2 mg/ml immunogen in 50% (v/v) FCA. Three sheep were immunised with this emulsion (1° immunisation), 0.25 ml being intramuscularly injected at each of four sites in the flank of each animal. Subsequent immunizations (boosts) contained 1 mg/ml immunogen. All boosts were emulsified in 50% (v/v) Freund's Incomplete Adjuvant (FIA) and were administered in the same manner as the 1° immunisation, at monthly intervals. Blood sampling took place 7 to 14 days after each boost.

Blood Collection

Briefly, blood is collected by applying pressure to the exposed jugular vein and inserting a clean 14 gauge hypodermic needle to remove 500 ml of blood per sheep, under gravity. The blood is stored at 37° C. for a minimum of 1 hour before the clots are separated from the side of the centrifuge bottles using disposable 1 ml pipettes (ringing). The samples are stored at 4° C. overnight.

Processing & Extraction of Immunoglobulin (Ig) Fraction:

Samples are centrifuged at 4000 g for 30 minutes at 4° C. The serum is then poured off and centrifuged again at 16,000 g for 15 minutes at 4° C., before being aliquoted and stored at <−20° C.

Precipitation of IgG from polyclonal antisera is carried out in two steps, using caprylic acid initially to precipitate most of the non-Ig G proteins, including albumin, followed by ammonium sulphate to extract IgG from the supernatant. This method produces a highly purified IgG fraction.

8 ml of 60 mM sodium acetate buffer, pH 4.4 is added to 2 ml of antisera, followed by the addition of 200 µl of caprylic acid. The resulting mixture is mixed on a roller for 30 minutes at room temperature. The precipitate is removed by centrifuging the samples at 1000 g for 20 minutes at 4° C. and filtering the supernatant through a 0.2 µm Acrodisc™ filter. 1.4 ml of 0.5M carbonate-bicarbonate buffer, pH 10.7, is added to each sample supernatant and cooled to 4° C. 9 ml of saturated ammonium sulphate solution is added slowly whilst shaking and the resulting mixture is placed on a roller for 30 minutes at room temperature. The precipitate is extracted by centrifuging the samples at 1000 g for 35 minutes at 4° C. The supernatant is poured off and the pellet re-suspended in 2 ml PBS, pH 7.2. The sample is dialysed overnight at 4° C. in PBS, pH7.2 containing 0.09% azide. After dialysis, the sample is filtered using a 0.2 µm Acrodisc™ filter and aliquoted for storage at <20° C. The IgG fraction can then be evaluated by competitive ELISA microtiter plate assay, as described below.

Example 12

Characterisation of Antibodies to Immunogen 2b (CP47,497-$C_8$)

Standard Curves

The wells of an enhanced binding 96 well polystyrene microtiter plate were coated with IgG fraction of antiserum (Antibody 4.1 or antibody 4.2) raised to Immunogen 2b in separate host animals, diluted in 10 mM Tris, pH8.5 (125 µl/well). The appropriate antibody coating dilution was determined using standard ELISA checkerboard techniques. The plate was incubated overnight at 4° C., washed 4 times over 10 minutes with Tris buffered saline containing Tween 20 (TBST) and tapped dry.

Standard solutions of CP47,497-$C_8$ were prepared in TBST at 0, 2.5, 5, 10, 20, 40, 80 and 160 ng/ml for Antibody 4.1, and at 0, 5, 10, 20, 40, 80, 160 and 320 ng/ml for Antibody 4.2, and 50 µl of each was added to the appropriate wells. 75 µl of conjugate (Hapten 1-HRP—tracer 1—see FIG. 4) diluted in Tris buffer (pH 7.2) containing EDTA, D-mannitol, sucrose, thimerosal and BSA, was added to each of the wells. The appropriate dilution of conjugate was also determined using standard ELISA checkerboard techniques. The plate was incubated at 25° C. for 1 hour. Excess unbound conjugate was removed by washing 6 times over a 10 minute period with TBST. 125 µl of tetramethylbenzidine (TMB) substrate solution was added to each well of the plate that was then incubated for 20 minutes in the dark at room temperature. The reaction was terminated by addition of 125 µl 0.2M $H_2SO_4$ to each well. The absorbance was then measured at 450 nm using a microtiter plate reader. The data generated in the assay is presented in Table 1.

TABLE 1

Data generated from competitive microtiter plate assays for CP47,497 - $C_8$, employing antisera raised against Immunogen 2b ($C_8$) (antibody 4.1 in Table 1a and antibody 4.2 in Table 1b), tracer 1 ($C_7$) and, as standard, (±)-CP-47,497 ($C_8$ homologue).

Table 1a -

| CP47,497 ($C_8$) | Antibody 4.1 | |
|---|---|---|
| ng/ml | $A_{450}$ | % $B/B_0$ |
| 0 | 1.866 | 100 |
| 2.5 | 1.529 | 82 |
| 5 | 1.339 | 72 |
| 10 | 1.117 | 60 |
| 20 | 0.945 | 51 |
| 40 | 0.808 | 43 |
| 80 | 0.700 | 38 |
| 160 | 0.641 | 34 |
| $IC_{50}$ (ng/ml) | 20.922 | |

Table 1b

| CP47,497 ($C_8$) | Antibody 4.2 | |
|---|---|---|
| ng/ml | $A_{450}$ | % $B/B_0$ |
| 0 | 1.877 | 100 |
| 5 | 1.657 | 88 |
| 10 | 1.546 | 82 |
| 20 | 1.356 | 72 |
| 40 | 1.184 | 63 |
| 80 | 0.979 | 52 |
| 160 | 0.827 | 44 |
| 320 | 0.698 | 37 |
| $IC_{50}$ (ng/ml) | 95.992 | |

$A_{450}$ = absorbance at 450 nm
B = absorbance at 450 nm at xng/ml standard concentration
$B_0$ = absorbance at 450 nm at 0 ng/ml standard concentration
$IC_{50}$ = standard concentration which produces 50% B/B Antibody 4.2 shows a higher $IC_{50}$ than antibody 4.1. This is reflected in their respective titres (not shown). Antibody 4.2 may show a lower $IC_{50}$ when purified from subsequent immunisations from the same host animal. In the next experiment, each of antibodies 4.1 and 4.2 show a similar cross-reactivity pattern.

Cross Reactivity

In order to determine the specificity of the competitive ELISAs, standard solutions of a range of structurally similar compounds were prepared in TBST. Using the calibration curves generated and employing a single level of cross reactants (100 ng/ml), these were used to determine the cross-reactivity of each immunoassay with these substances. The results of this study are presented in Table 2, as % $B/B_0$, employing antisera raised against Immunogen 2b ($C_8$), tracer 1 ($C_7$) and (±)-CP-47,497 ($C_8$ homologue) as standard.

TABLE 2

| | Cross-reactants at 100 ng/ml | Antibody 4.1 % $B/B_0$ | Antibody 4.2 % $B/B_0$ |
|---|---|---|---|
| 1 | (±)-CP-47,497 ($C_7$ homologue) | 37.14 | 48.85 |
| 2 | (±)-CP-47,497 ($C_7$ para quinone analogue), identified as "cayman 10899" | 82.66 | 89.82 |
| 3 | (±)-CP-47,497 ($C_8$ homologue) | 36.52 | 49.65 |
| 4 | ((+−)-CP 55,940)—CAS No. 83003-12-7 | 93.65 | 97.34 |
| 5 | (−)-CP 55,940—CAS No. 83002-04-4 | 91.26 | 97.23 |
| 6 | (+)-CP 55,940, identified as "cayman 13608" | 95.98 | 96.91 |
| 7 | HU-210—CAS No. 112830-95-2 | 96.01 | 92.94 |
| 8 | HU-211 (Dexanabinol)—CAS No. 112924-45-5 | 96.76 | 95.84 |
| 9 | HU-308—CAS No. 256934-39-1 | 98.37 | 94.81 |
| 10 | Delta 9 THC—CAS No. 1972-08-3 | 96.44 | 94.09 |
| 11 | (−)-11-nor-9-Carboxy-delta9-THC—CAS No. 56354-06-4 | 95.23 | 94.38 |

Figure 5:
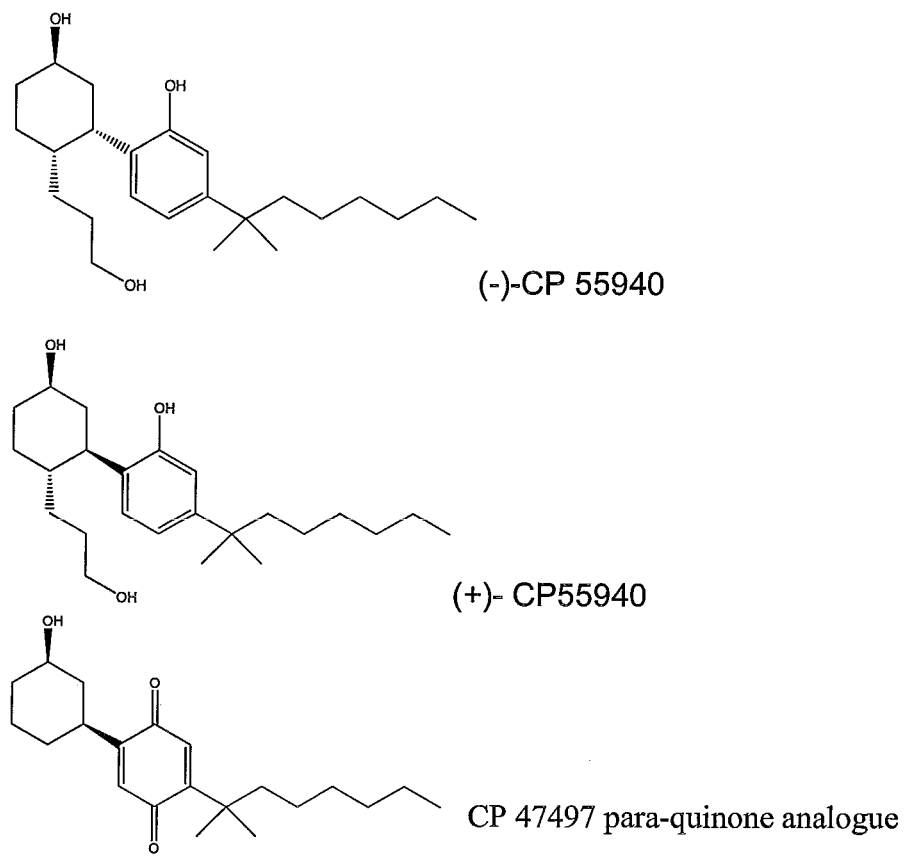
FIG. 5 contains diagrams of chemical structures of (−)-CP 55940, (+)-CP55940 and CP 47497 para-quinone analogue.

(+)- CP55,940 and (−)- CP55940 are illustrated in FIG. 5 and provided by Cayman Chemicals.
((+−)-CP 55,940) is a racemic mixture of (+)- CP55940 and (−)- CP55940.
(±)-CP-47,497 ($C_7$ para quinone analogue) is also illustrated in FIG. 5. Each of (±)-CP-47,497 ($C_7$ homologue) and (±)-CP-47,497 ($C_8$ homologue) is a mixture of the 2 possible cyclohexyl cis configurations.

Cross-reactivity is calculated according to the following formula:

% CR=$IC_{50, CP47, 497 (C8)}$/$IC_{50, CR}$×100

Where % CR is the percentage cross-reactivity, $IC_{50, CP47, 497 (C8)}$ is the concentration of CP47, 497 ($C_8$) that causes 50% displacement of signal and $IC_{50, CR}$ is the concentration of CP synthetic cannabinoid/metabolite/selected molecule that causes 50% displacement of signal.

The cross-reactivity data show that antibodies raised against immunogen 2b bind to each of (±)-CP-47,497 ($C_7$ homologue) and (±)-CP-47,497 ($C_8$ homologue)—these antibodies show a % $B/B_0$ of less than 50% with each of these cross-reactants, using tracer 1 ($C_7$) and (±)-CP-47,497 ($C_8$ homologue) as standard. A similar % $B/B_0$ of less than 50% is also expected for each stereoisomer in the racemic mixture forming each of (±)-CP-47,497 ($C_7$ homologue) and (±)-CP-47,497 ($C_8$ homologue). In contrast, antibodies raised against immunogen 2b show a % $B/B_0$ of greater than 80% with each of ((+−)-CP 55,940), (−)-CP 55,940 and (+)-CP 55,940. It will be appreciated that, in CP-47,497, there is a hydroxyl substituent at position 3 of the cyclohexane ring and hydrogen substituents at the 6 position. In contrast, in CP-55,940, there remains a hydroxyl substituent at position 3 of the cyclohexane ring but one of the hydrogen substituents at the 6 position is replaced by a propyl group terminating in a hydroxyl group. It would appear that antibodies raised against immunogen 2b require 2 hydrogen substituents at position 6 of the cyclohexyl ring.

In (±)-CP-47,497 ($C_7$ para quinone analogue), the phenyl ring of (±)-CP-47,497 ($C_7$ homologue) is replaced by a p-benzoquinone ring. Antibodies raised against immunogen 2b show a % $B/B_0$ of greater than 80% with (±)-CP-47,497 ($C_7$ para quinone analogue). It would appear that antibodies raised against immunogen 2b require a hydrogen substituent at position 4 of the phenyl ring.

In HU-210 and HU-211, there is an additional ring bridging position 6 of the cyclohexyl ring and position 3 of the phenyl ring. Antibodies raised against immunogen 2b show a % $B/B_0$ of greater than 80% with each of HU-210 and HU-211. It would appear that antibodies raised against immunogen 2b require a hydrogen substituent at position 3 of the phenyl ring and 2 hydrogen substituents at position 6 of the cyclohexyl ring.

The invention claimed is:
1. An antibody that binds to (±)-CP-47,497 ($C_7$ homologue) and (±)-CP-47,497 ($C_8$ homologue),
wherein the antibody has a cross-reactivity presented as $B/B_0$ of ≤50% against (±)-CP-47,497 ($C_7$ homologue) at a concentration of 100 ng/ml, and a cross-reactivity presented as $B/B_0$ of ≤50% against (±)-CP-47,497 ($C_8$ homologue) at a concentration of 100 ng/ml, and
wherein the antibody has a cross-reactivity presented as $B/B_0$ of greater than 80% against each one of the cross-reactants selected from the group consisting of (±)-CP-47,497 ($C_7$ para quinone analogue), (±)-CP-55,940, (−)-CP 55,940, (+)-CP 55, 940, HU-210, HU-211 (dexanabinol), HU-308, delta9-THC, and (−)-11-nor-9-carboxy-delta9-THC, at a cross-reactant concentration of 100 ng/ml,
as determined using (±)-CP-47,497 ($C_8$ homologue) as a standard and Tracer 1,
wherein Tracer 1 has the following structural formula:

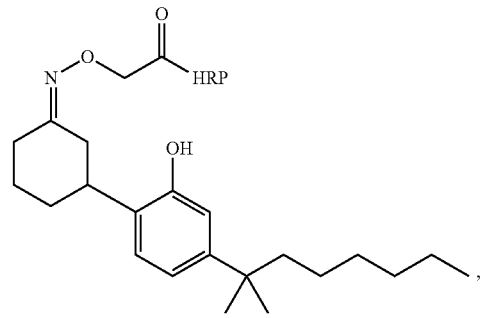

wherein HRP is Horse Radish Peroxidase,
wherein $B_0$ is absorbance at 450 nm at zero ng/ml standard concentration, and
wherein B is absorbance at 450 nm at predetermined variable standard concentrations.
2. An antibody raised against an immunogen of the following structure:

Group II (e)

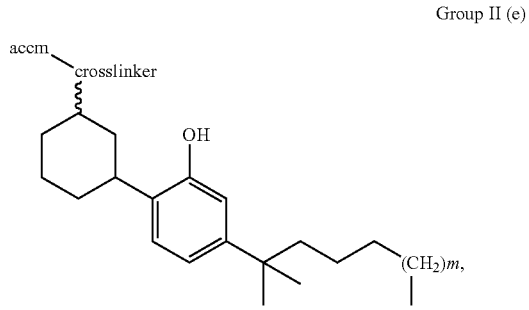

wherein the accm is an antigenicity conferring carrier material;

wherein the crosslinker is a functionalised linking group joining the accm to the remainder of the molecule, the crosslinker forming a double bond to the cyclohexyl ring;

wherein m is 3;

wherein the antibody has a cross-reactivity presented as $B/B_0$ of $\leq 50\%$ against ($\pm$) CP-47,497 ($C_7$ homologue) at a concentration of 100 ng/ml and a cross-reactivity presented as $B/B_0$ of $\leq 50\%$ against ($\pm$)-CP-47,497 ($C_8$ homologue) at a concentration of 100 ng/ml, and wherein the antibody has a cross-reactivity presented as $B/B_0$ of greater than 80% against each one of the cross-reactants selected from the group consisting of ($\pm$)-CP-47,497 ($C_7$ para quinone analogue), ($\pm$)-CP-55,940, (−)-CP 55,940, (+)-CP 55, 940, HU-210, HU-211 (dexanabinol), HU-308, delta9-THC, and (−)-11-nor-9-carboxy-delta9-THC, at a cross-reactant concentration of 100 ng/ml, wherein the $B/B_0$ is measured using ($\pm$)-CP-47,497 ($C_8$ homologue) as a standard and Tracer 1 as a tracer, of the following structural formula:

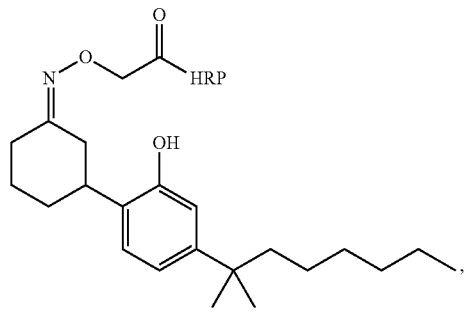

wherein $B_0$ is absorbance at 450 nm at zero ng/ml standard concentration, and wherein B is absorbance at 450 nm at predetermined variable standard concentrations.

* * * * *